United States Patent
Laugerette et al.

(10) Patent No.: US 12,300,369 B2
(45) Date of Patent: May 13, 2025

(54) SYSTEM AND METHOD FOR REPORTING ON MEDICAL IMAGES

(71) Applicant: Smart Reporting GmbH, Munich (DE)

(72) Inventors: Alexis Laugerette, Munich (DE); Wieland Sommer, Munich (DE)

(73) Assignee: SMART REPORTING GMBH, Munich (DE)

( * ) Notice: Subject to any disclaimer, the term of this patent is extended or adjusted under 35 U.S.C. 154(b) by 275 days.

(21) Appl. No.: 17/634,964

(22) PCT Filed: Aug. 12, 2019

(86) PCT No.: PCT/EP2019/071606
§ 371 (c)(1),
(2) Date: Feb. 12, 2022

(87) PCT Pub. No.: WO2021/028018
PCT Pub. Date: Feb. 18, 2021

(65) Prior Publication Data
US 2022/0336071 A1 Oct. 20, 2022

(51) Int. Cl.
*G16H 15/00* (2018.01)
*G16H 30/20* (2018.01)
(Continued)

(52) U.S. Cl.
CPC ............ *G16H 15/00* (2018.01); *G16H 30/20* (2018.01); *G16H 30/40* (2018.01); *G16H 70/20* (2018.01)

(58) Field of Classification Search
CPC ........ G16H 15/00; G16H 30/20; G16H 30/40; G16H 70/20
See application file for complete search history.

(56) References Cited

U.S. PATENT DOCUMENTS 8,643,680 B2 * 2/2014 Baldwin ................. G06F 3/013
345/581
9,280,818 B2 * 3/2016 Fukatsu ................. G16H 15/00
(Continued)

FOREIGN PATENT DOCUMENTS

JP  2015095043 A  *  5/2015
JP  5944326 B2  *  7/2016  ............. G06F 1/163
(Continued)

OTHER PUBLICATIONS

JP-2015095043-A—translated (Year: 2015).*
(Continued)

*Primary Examiner* — Jason S Tiedeman
*Assistant Examiner* — Jonathan C Edouard
(74) *Attorney, Agent, or Firm* — QUARLES & BRADY LLP

(57) ABSTRACT

The invention relates to a system, a corresponding method and a corresponding computer program product for reporting on medical images. The system comprises: means (1) for receiving one or more medical images (3), means (5) for receiving and/or creating a machine-readable structured report (7), an image display (9) configured to display the received one or more medical images (3), a report display (13) configured to display the received and/or created machine-readable structured report (7), means (17) for providing a floating user-interface (UI) window (19), and means (23) for updating and/or filling structured-report elements (25) of the received and/or created machine-readable structured report (7). The system is configured to identify and follow the focus of a user of the system and, based on the identified focus, to assign a section of the image display (9) as an active image-display section (27). The means for providing a floating UI window (17) are configured to position the floating UI window (19) in proximity of the active image-display section (27). The means for providing a floating UI window (17) are further configured to (i) display context-dependent content (33) within the floating UI window (17) and/or (ii) to allow the user to select via the floating UI window (17) one or more next steps within a workflow of reporting on the received one or more medical images. The means for updating and/or filling structured-report elements (23) are adapted such that the structured (Continued)

report elements (25) are automatically updated and/or filled based on the one or more workflow steps selected by the user.

12 Claims, 16 Drawing Sheets

(51) Int. Cl.
  *G16H 30/40* (2018.01)
  *G16H 70/20* (2018.01)

(56) References Cited

U.S. PATENT DOCUMENTS

| | | | |
|---|---|---|---|
| 9,971,401 B2* | 5/2018 | Stafford | G06F 3/013 |
| 2010/0049740 A1* | 2/2010 | Iwase | G16H 10/60 |
| | | | 705/7.27 |
| 2010/0121658 A1 | 5/2010 | Kaminski | |
| 2013/0290826 A1* | 10/2013 | Niwa | G16H 30/20 |
| | | | 715/230 |
| 2017/0061099 A1 | 3/2017 | Sati | |
| 2019/0033964 A1* | 1/2019 | Kulkarni | G06F 3/04842 |
| 2019/0102986 A1* | 4/2019 | Nelson | G06F 3/04815 |
| 2019/0204993 A1* | 7/2019 | Bastide | G06F 3/0481 |
| 2019/0214118 A1* | 7/2019 | Reicher | G16H 10/60 |
| 2019/0220978 A1* | 7/2019 | Moehrle | G06T 7/0014 |

FOREIGN PATENT DOCUMENTS

| | | | | |
|---|---|---|---|---|
| WO | WO-2018202482 A1 * | 11/2018 | | G06K 9/325 |
| WO | WO-2018222018 A1 * | 12/2018 | | G06F 3/011 |

OTHER PUBLICATIONS

JP5944326B2—translated (Year: 2016).*
International Search Report of International Application No. PCT/EP2019/071606, mailed Mar. 31, 2020, 3 pages.
Written Opinion of International Application No. PCT/EP2019/071606, mailed Mar. 31, 2020, 6 pages.

* cited by examiner

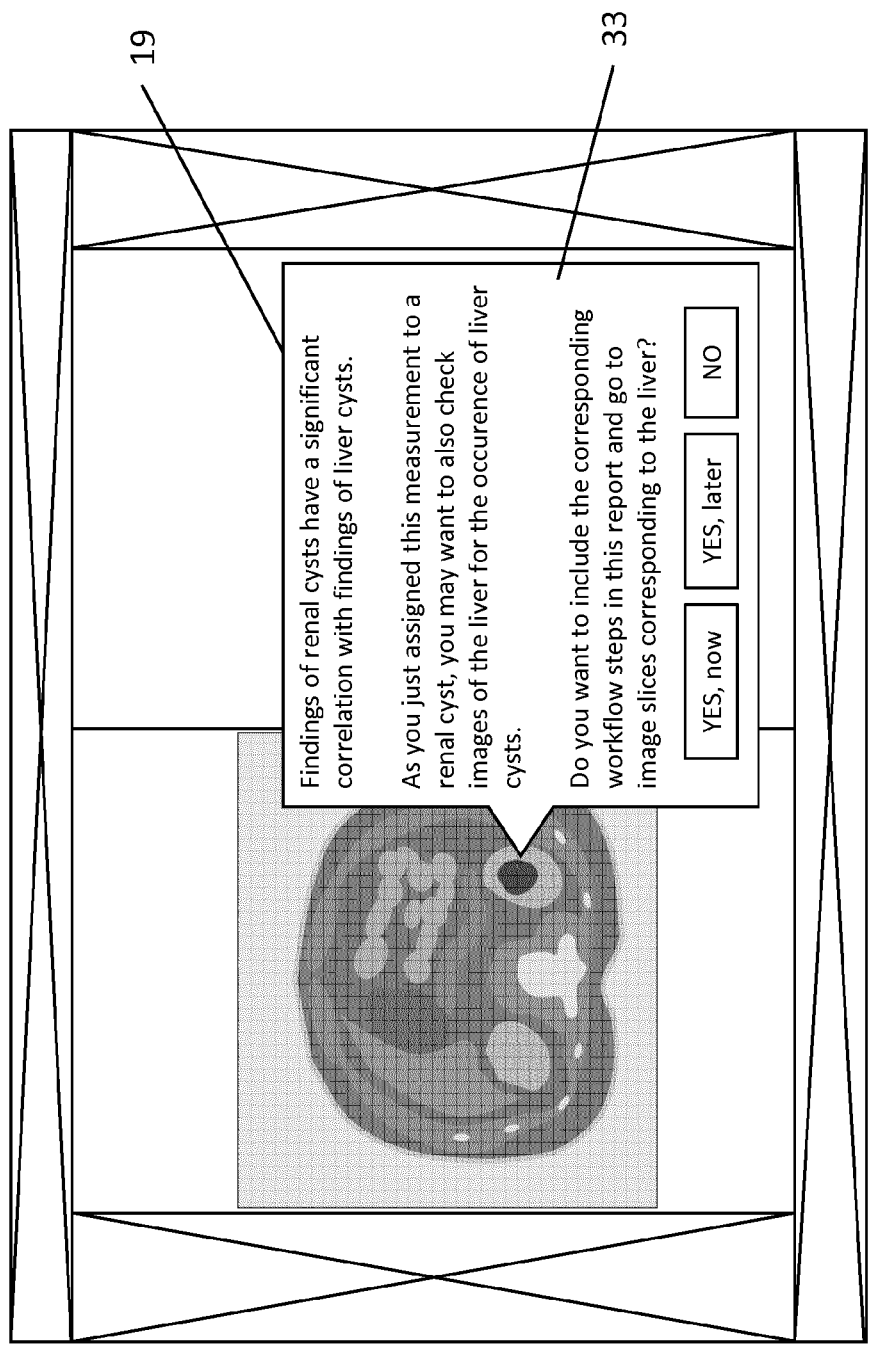

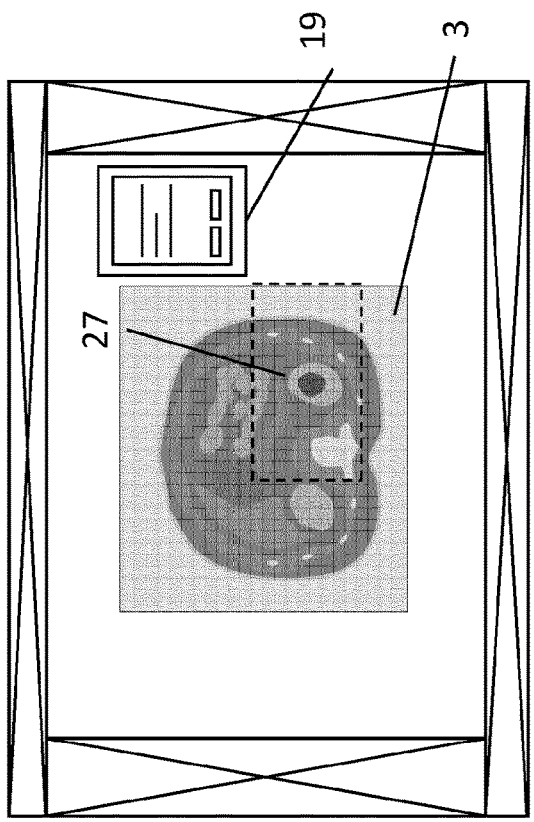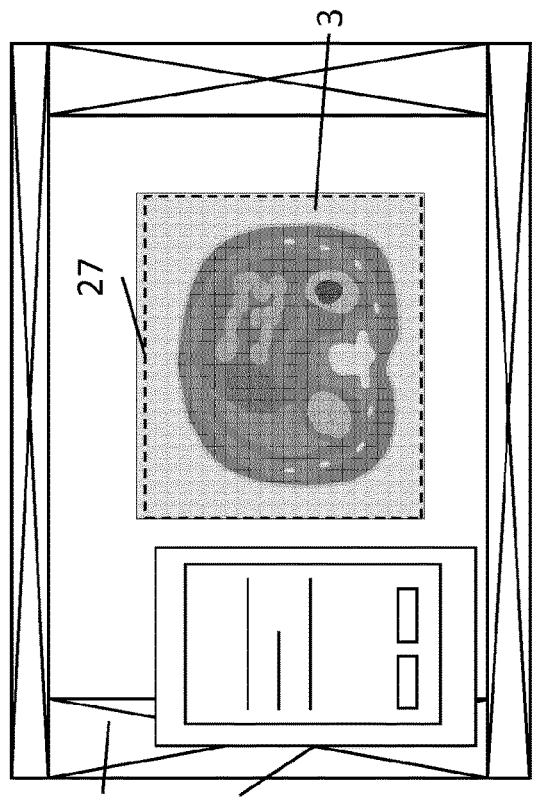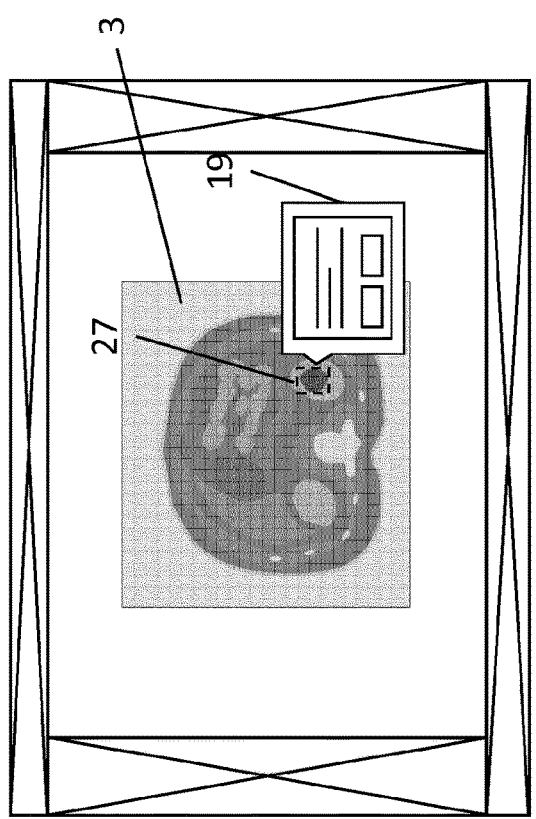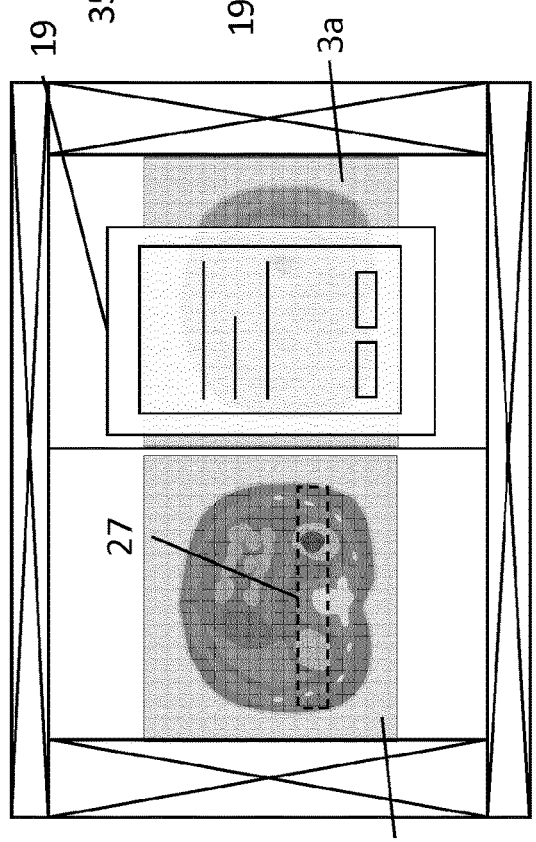

SYSTEM AND METHOD FOR REPORTING ON MEDICAL IMAGES

CROSS-REFERENCE TO RELATED APPLICATIONS

This application represents the U.S. national stage entry of PCT International Application No. PCT/EP2019/071606 filed Aug. 12, 2019. The contents of this application are hereby incorporated by reference as if set forth in their entirety herein.

BACKGROUND OF THE INVENTION

The present invention concerns systems and methods for reporting on medical images and in particular for producing machine-readable structured reports.

In a report, a reviewing physician, e.g., a radiologist, summarizes, typically in writing, the observations that the reviewing physician makes when reviewing medical images. In a first step, a typical radiology report is done organ by organ. E.g., in a CT of the thorax the radiologist is looking, beyond others, at the heart, pericardium, lung parenchyma and airways. In a subsequent step, the radiologist summarizes the main findings into an impression. The main findings of a report contain so-called key findings which indicate remarkable aspects found in the images.

The report can be free-text. Then, its structure, elements, style, wording and layout differ from physician to physician. They are not machine-readable, not standardized, and not analyzable. Moreover, they are prone to artefacts and they might be unclear or even incomplete.

To overcome the drawbacks of free-text reports, so-called structured reports were introduced. These are based on structured, machine-readable reporting templates that can be progressively filled in by radiologists. Ideally, a structured report is machine-readable, has a fixed structure and contains standardized elements, wording and layout.

In a typical workflow for generating a report, a reviewing physician looks at radiological images on two, or sometimes even more, monitors, typically on her or his right. The physician eventually makes some measurements in the images, thinks about a potential classification of a condition and eventually seeks help in textbooks, guidelines or the internet. Finally, the reviewing physician writes the corresponding report in a reporting application which is usually displayed on a third monitor, usually on her or his left side. The reviewing physician typically navigates within and/or between the images using a computer mouse. In parallel, the reviewing physician works on the report using a keyboard and a mouse for typing and/or a microphone and a mouse for dictating. Potentially, these steps are repeated many times.

However, this workflow is not optimal: every time a finding must be added to the report, the eyes and head of the radiologist switch back and forth between the screens or windows, i.e. the images and the report. This constant switching is physically and mentally fatiguing which eventually leads to loss of focus and reduces concentrativeness. Due to the non-optimal ergonomics of this process, the reporting process becomes prone to errors.

The ergonomics further worsens when reporting on follow-up examinations, i.e., examinations of a patient who was already examined at least once before and which regards a potential pathological finding that was found during this previous examination. A considerable amount of radiology reports concerns such follow-up examinations. For those, the radiologist firstly has to read the one or more previous reports and to extract the key findings. Then the radiologist needs to shift his or her focus to the associated images of the previous examination, and, finally, to the corresponding images of the current examination. Thus, for a follow-up task, the radiologist basically starts from scratch every time. These additional steps increase the duration of the reporting process. Also, these steps further impair the ergonomics of the reporting process and, therefore, render the reviewer's workflow even more error-prone.

If, in addition, the reviewing physician needs to compare findings in the two sets of images, he or she may have to repeat measurements that were already performed for the previous report. Given that a previous measurement was usually carried out some time ago and/or by a different person, it is difficult to accurately repeat this measurement. However, carrying out measurements differently and comparing the results of those measurements introduces an additional intra- and/or inter-operator bias. The comparison and eventually the resulting conclusions become inaccurate. This renders the workflow of a follow-up task even more error-prone, time-consuming and inefficient.

The need to improve the workflow of reviewing physicians was recognized by the state of the art.

US 2018/0060533 A1 describes systems and methods for automatically transferring image annotations from electronic medical images to a structured report. The anatomical location within the electronic medical image and, based on a predetermined mapping, also the location within the electronic structured report is determined and populated automatically.

US 2018/0240537 A1 (EP 3271844 A1) describes an apparatus and a method for generating a structured report and guiding a clinician to unaddressed aspects of the report. To this end, suggested finding codes are generated and displayed based on physiological information. The adopted finding codes are then used to generate and display a structured report.

US 2017/0061099 A1 describes methods and systems for using contextual information to generate reports for imaging studies. Based on contextual information a discrete data element for a structured report and/or a vocabulary for natural language processing engine may be determined. Examples for contextual information include image type, number of images included in the imaging study, Digital Imaging and Communications in Medicine ("DICOM") header information or the hanging protocol associated with the imaging study.

US 2014/0379364 A1 describes a method and computer apparatus to automatically populate fields of an electronically formatted structured report depending on the level of experience of the user. The level of experience may, for example, be determined based on the number of years that the clinician has been practicing for. The higher the identified level of experience, the more sub-sets of fields of the electronically formatted structured report are populated automatically.

US 2005/0273365 A1 (EP 1763812 A2) describes methods and systems for creating and sharing structured reports. These include a business logic server and a structured object repository configured to hold a plurality of structured report templates which are based on a common schema.

Against this background, there is a need to further improve the workflow and ergonomics of physicians while reviewing medical images. This improves the accuracy and completeness of medical reports, enhances the efficiency of the reporting process and eventually results in better subsequent diagnosis of diseases and treatment of patients.

SUMMARY OF THE INVENTION

The invention further improves the workflow and ergonomics of physicians while reviewing medical images by providing systems and methods for reporting on medical images.

According to one aspect, a system for reporting on medical images is provided. The system comprises:
  means for receiving one or more medical images,
  means for receiving and/or creating a machine-readable structured report,
  an image display configured to display the received one or ore medical images,
  a report display configured to display the received and/or created machine-readable structured report,
  means for providing a floating user-interface (UI) window, and
  means for updating and/or filling structured-report elements of the received and/or created machine-readable structured report.

The system is configured to identify and follow the focus of a user of the system. Based on the identified focus, the system is further configured to assign a section of the image display as an active image-display section.

The means for providing a floating UI window are configured to position the floating UI window in proximity of the active image-display section.

The means for providing a floating UI window are further configured to
  (i) display context-dependent content within the floating UI window and/or
  (ii) to allow the user to select via the floating UI window one or more next steps within a workflow of reporting on the received one or more medical images.

The means for updating and/or filling structured-report elements are adapted such that the structured report elements are automatically updated and/or filled based on the one or more workflow steps selected by the user.

According to another aspect, a method for reporting on medical images is provided. The method comprises the following steps:
  a) receiving one or ore medical images,
  b) receiving and/or creating a machine-readable structured report,
  c) displaying the received one or more medical images in an image-display,
  d) displaying the received and/or created machine-readable structured report in a report-display,
  e) providing a floating user-interface (UI) window, and
  f) updating and/or filling structured-report elements of the received and/or created machine-readable structured report.

The method further comprises:
  identifying and following the focus of a user of the method and, based on the identified focus, assigning a section of the image display as an active image-display section;
  positioning the floating UI window in proximity of the active image-display section;
  displaying context-dependent content in the floating UI window;
  allowing the user to select via the floating UI window one or more next steps within a workflow of reporting on the received one or more medical images; and
  automatically updating and/or filling the structured-report elements based on the workflow steps selected by the user.

According to another aspect, a computer program product stored on a non-transitory storage medium is provided. The computer program product comprises computer readable instructions to execute the steps of the above described method.

The foregoing and other advantages will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 11 illustrates an exemplary embodiment of a system for reporting on medical images where, based on identified findings, one or more selectable next workflow steps as well as suggestions for potential other findings are provided to the user via the floating UI window;

FIGS. 12a-12d schematically show examples of floating UI windows that do not cover or overlap with the active image-display section;

DETAILED DESCRIPTION

Figure 1:
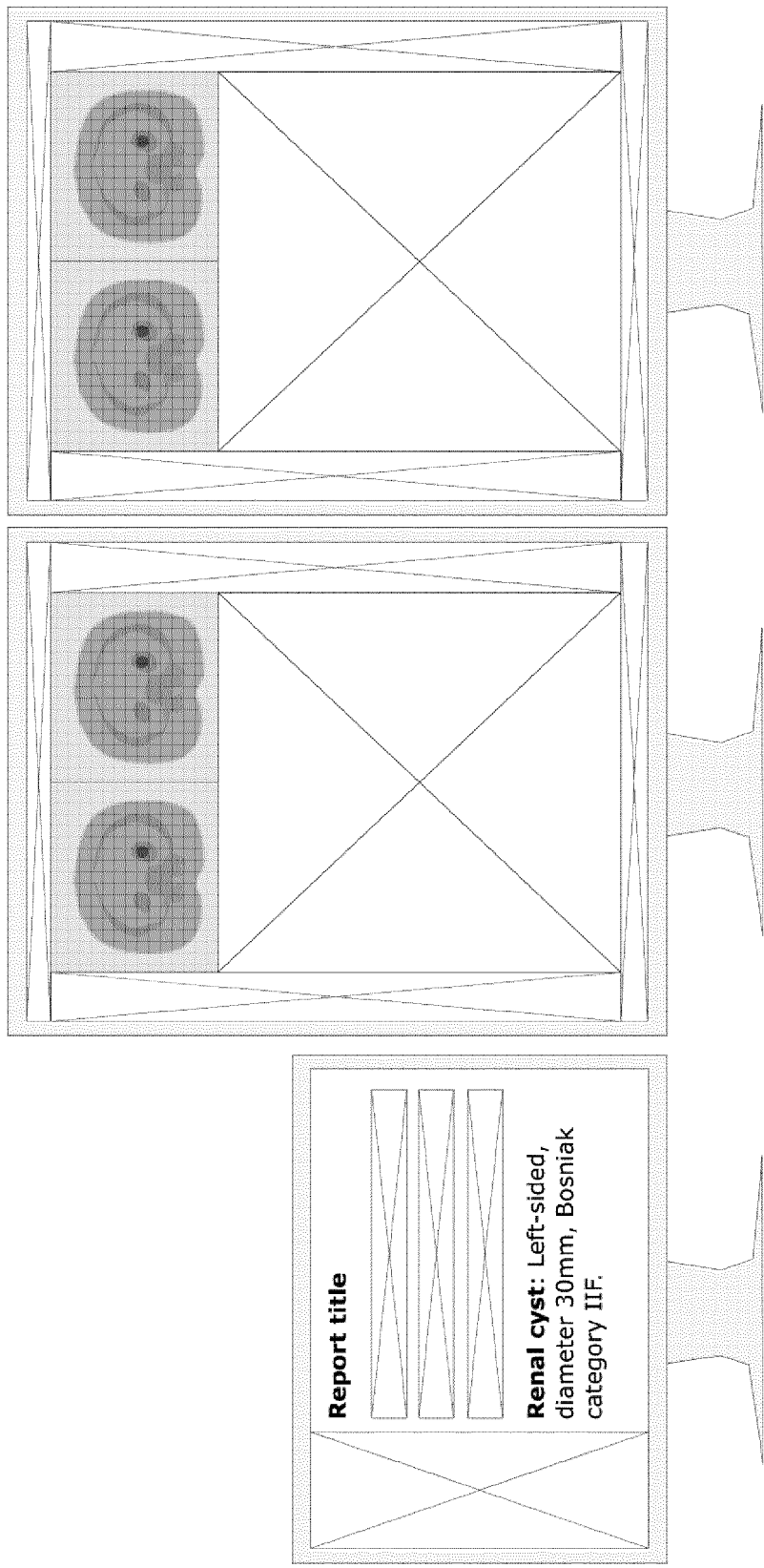
FIG. 1 schematically illustrates an example of a typical configuration of a radiologist's workspace.

The workstation of a reviewing physician typically comprises several displays for displaying medical images, reports and further information on a patient. FIG. 1 schematically depicts an example workstation that uses two computer monitors as image displays 9 and one computer monitor as report display 13. Before going into the details of FIG. 1, some general aspects regarding preferred embodiments of the invention are discussed.

In accordance with preferred embodiments of the invention, methods for reporting on medical images or systems with correspondingly configured components for reporting on medical images are provided. The methods and systems comprise the following steps or components for carrying out these steps:
 receiving one or more medical images,
 receiving and/or creating a machine-readable structured report 7,
 displaying the received one or more medical images 3 in an image-display 9,
 displaying the received and/or created machine-readable structured report 7 in a report-display 13,
 providing a floating user-interface (UI) window 19, and
 updating and/or filling, structured-report elements 25 of the received and/or created machine-readable structured report 7.

Furthermore, the methods and systems comprise the following steps or components for carrying out these steps:
 identifying and following the focus of a user of the method and, based on the identified focus, assigning a section of the image display 9 as an active image-display section 27;
 positioning the floating UI window 17 in proximity of the active image-display section 27;
 displaying context-dependent content 33 in the floating UI window 17;
 allowing the user to select via the floating UI window 19 one or more next steps within, a workflow of reporting on the received one or more medical images; and
 automatically updating and/or filling the structured-report elements 25 based on the workflow steps selected by the user.

The skilled person understands that the mentioned steps do not have to be performed in the order as they appear above or in the appended claims but are rather exemplary only. Different sequences of these steps may well be suitable and even preferable depending on the circumstances of the work environment in which the physician is embedded. For example, the machine-readable structured report 7 may also be received before the one or more medical images 3 are received. Furthermore, the one or more medical images 3 may be displayed directly after receiving them and the machine-readable structured report 7 may be displayed directly after its reception and/or creation. The floating UI window 19 may also be displayed after identifying and following the focus of the user. Furthermore, the context dependent content 33 may be displayed directly after providing the floating UI window 19 and the floating UI window 19 may also be positioned in proximity of the active image-display section 27 after the context dependent content 33 is displayed in the floating UI window 19.

In general, the one or more medical images 3 and/or the machine-readable structured report 7 can be received from several sources. Examples for such sources for medical images 3 and/or machine-readable structured reports 7 include data repositories like a picture archiving and communication system (PACS), a radiology information system (RIS), a hospital information system (HIS), and an electronic medical record (EMR). Further examples include databases that are stored on a server, locally on a computer and/or a storage medium. The medical images 3 and/or machine-readable structured reports 7 may also be obtained directly from an imaging system, e.g., a computer tomography (CT)- or magnetic resonance imaging (MRI)-scanner. Also, combinations of the above databases and repositories as well as other systems can be used to store and/or access medical images 3 and/or machine-readable structured reports 7.

In principle, more than one image display 9 can be used. The image display 9 may, as a non-limiting example, be included in a proprietary viewer, PACS or other viewing system.

Also, more than one report display 13 can be used. The report display 13 may, as a non-limiting example, be included in a proprietary viewer, RIS or other viewing or display system.

Finally, also more than one floating UI window 19 can be generated which may or may not be displayed simultaneously.

Examples for medical images 3 include, but are not limited to, X-Ray, magnetic resonance (MR)-, CT-, ultrasound-, positron emission tomography (PET)- and/or single photon emission computed tomography (SPECT)-images, digital pathology pictures from a microscope, e.g., of tissue samples, and/or images of other suitable imaging modalities. Combinations of medical images generated by different imaging modalities, e.g. overlays of PET- and MR-images, are further non-limiting examples for the medical images 3. The term medical images 3 includes a single image as well as a set of several images, e.g. slices of a 2D or 3D multi-slice MR-acquisition or a set of images provided by different modalities mentioned above, for example a prostate MRI scan and the corresponding digital pathology microscope-images.

Non-limiting examples of structured-report elements 25 include graphical elements with selectable/drawable regions, text fields, text elements, numerical values, logical values, boolean values, tables, single-selection elements, multi-selection elements and/or image snapshots.

In principle, the structured-report elements 25 can also contain links. This way, the structured-report elements and/or their content can be linked to the medical images 3 and/or annotations like measurements or findings that they are associated with. For example, a link in form of an image snapshot, text or other information corresponding to a detected lesion might be automatically added to a structured-report element 25. This link is displayed in the machine-readable structured report 7 and can be used to go back to the corresponding location in the displayed medical images 3. For example, by clicking on the report's text or image snapshot corresponding to a lesion, the user can go back to the image display 9 that already shows the medical image 3, slice and/or region of interest (ROI) associated with the lesion's link in the machine-readable structured report 7. Particularly in follow-up reports, this facilitates the identification and retrieval of findings mentioned in previous machine-readable structured reports. Annotations include, but are not limited to, manual measurements of, e.g., length, area, volume, angle, intensity, density, mean Hounsfield Units (HU), ROIs, and/or ROI properties. Annotations further include results and/or findings that are manually determined or suggested via artificial intelligence (AI) enabled detection. Annotations also include combinations of types of annotations, e.g., those mentioned above. Also, annotations include calculating parameter values from other values, e.g. results of measurements. If applicable to the type of annotations, these can be displayed within medical images 3, e.g., via colored overlays, heatmaps, graphical elements and/or other types of information representation.

The context dependent content 33 is in general determined by the medical images 3 and/or the machine-readable structured report 7. The context-dependent content 33 may additionally or alternatively be determined by previous machine-readable structured reports, annotations in previous medical images and/or other workflow steps carried out during reporting on current or previous medical images. The context dependent content 33 can provide selectable items that, e.g., allow the user to perform one or more workflow steps and/or generate one or more annotations. The context dependent content 33 may further provide information relevant for reporting on medical images, for example display relevant guidelines and classifications for the current reporting task. Also, the context dependent content 33 can depend on the workflow steps that were performed during the current process of reporting. Steps that were performed as part of the workflow of reporting on medical images 3 can also trigger providing further floating UI windows 19 with corresponding context dependent content 33.

In general, one or more floating UI windows 19 may be displayed for instance after an annotation was made in an image, i.e., triggered by generating the annotation. However also other triggers are possible such as user interaction with the computer mouse or a touch-sensitive display, user interaction with microphone or voice recording device buttons, or voice commands. The context-dependent content 33 of the floating UI windows 19 then enables a selection of items to be automatically transferred to the report. This may require information of a localization within the image, which can be provided, e.g., by using standard coarse organ segmentation algorithms.

In general, in an image display 9 one or more image-display sections can be defined. This may require information of a localization within the medical image 3, which can be provided, e.g., by using standard coarse organ segmentation algorithms.

Such image-display sections can be in an active or non-active state. As a non-limiting example, an image-display section can be assigned to be in an active state when the focus of a user is on that specific image-display section. Examples of indicators for an active state of an image-display section include, but are not limited to, the current position of a cursor. If the cursor is inside an image-display section, the focus of a user is regarded to be on that image-display section and an active state assumed, i.e., the image-display section is assigned to be an active image-display section 27. The cursor may, e.g., be controlled by a mouse, trackpad or via a touch-sensitive screen. Another example for an indicator for an active state, is based on the detection of actions that a user is currently carrying out inside a specific image-display section. A non-limiting example for such actions is generating one or more annotations. Yet another example for an indicator for an active state, is based on detecting if a user is currently looking at the respective image-display section. This can for example be detected via eye-tracking. The above described indicators and ways of detection can also be combined.

The floating UI windows 19 are displayed in proximity of the active image-display section 27. In other words, the position of the floating UI windows 19 is ideally as close as possible to the position of the active image-display section 27. This ensures that the user keeps her or his focus on, or at least close to, the active image-display section 27 while not concealing any parts of the image content or information that is relevant for the current workflow step. Depending on the scenario, the position of the floating UI window 19 can be next-to-next to an active image display section 27 or be at some distance to it.

In accordance to some embodiments of the invention, the findings in the medical images 3 can trigger calling modules that define structured-report elements 25 from report templates or adding them to the current report template (use case modular structured reporting). An aspect of this is, that the report, structure can be generated on the fly, i.e., be modified while reviewing the images. For example, a template for chest CT would include by default typical modules for the lungs, but the radiologist might want to report as well about the heart or spine, which could lead to other—not often used—modules to be added on the fly to the structure for this particular case.

Figure 2:
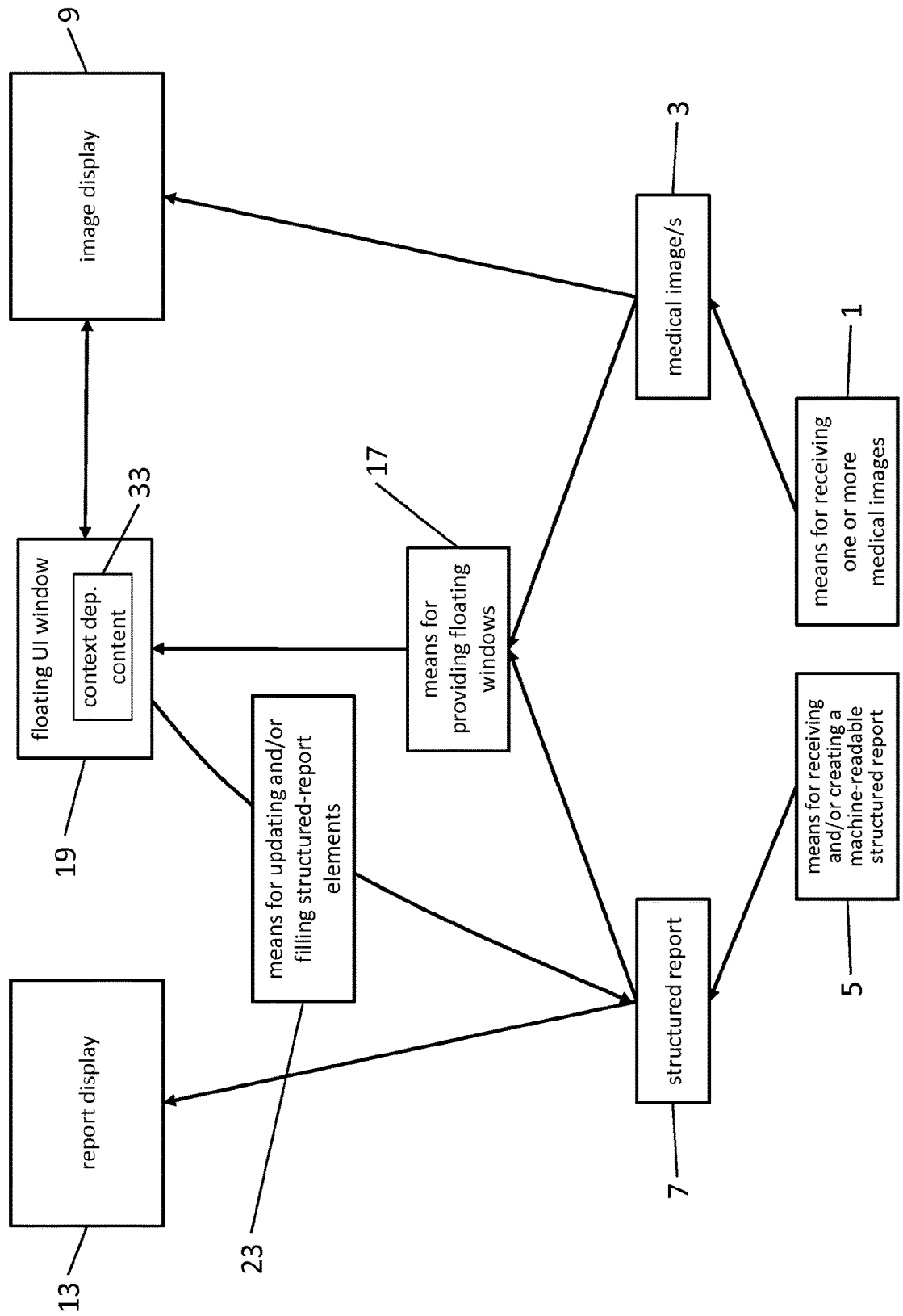
FIG. 2 schematically illustrates an exemplary embodiment of a system for reporting on medical images.

FIG. 2 schematically illustrates an example of a system.

Means for receiving medical images 1 receive or retrieve one or more medical images 3, e.g. from a data repository or directly from an imaging system, e.g., a PET-scanner.

The medical images 3 are displayed in the image display 9.

Means for receiving and/or creating a machine-readable structured report 5 provide a machine-readable structured report 7. To this end, the means for receiving and/or creating a machine-readable structured report 5 generate a new machine-readable structured report 7 and/or receive/retrieve an existing one, e.g. from a data repository.

The machine-readable structured report 7 is displayed in the report display 13. The machine-readable structured report 7 contains structured-report elements 25, that can be of any structured type as stored in a database or repository.

Means for providing a floating UI window 17 generate a floating UI window 19. The floating UI window 19 provides context-dependent content 33 which is determined by information identified in the machine-readable structured report 7 and/or the one or more medical images 3. In other embodiments, the context-dependent content may alternatively or in addition be determined by other information, e.g., identified in other clinical content like relevant guidelines.

Via the floating UI window 19, the user transfers information to the means for updating and/or filling structured-report elements 23. Based on this information, the means for updating and/or filling structured-report elements 23 update and/or fill the structured-report elements 25 of the machine-readable structured report 7. For example, text that is associated with one or more findings in one or more medical images 3 can be transferred to the machine-readable structured report 7 and its elements via the floating UI window 19 and the means for updating and/or filling structured-report elements 23. The radiologist then has the option to check from time to time if the report is as expected and modify its content (write, override, delete), either by adding or editing free-text, or by performing the changes in a structured form.

Figure 3:
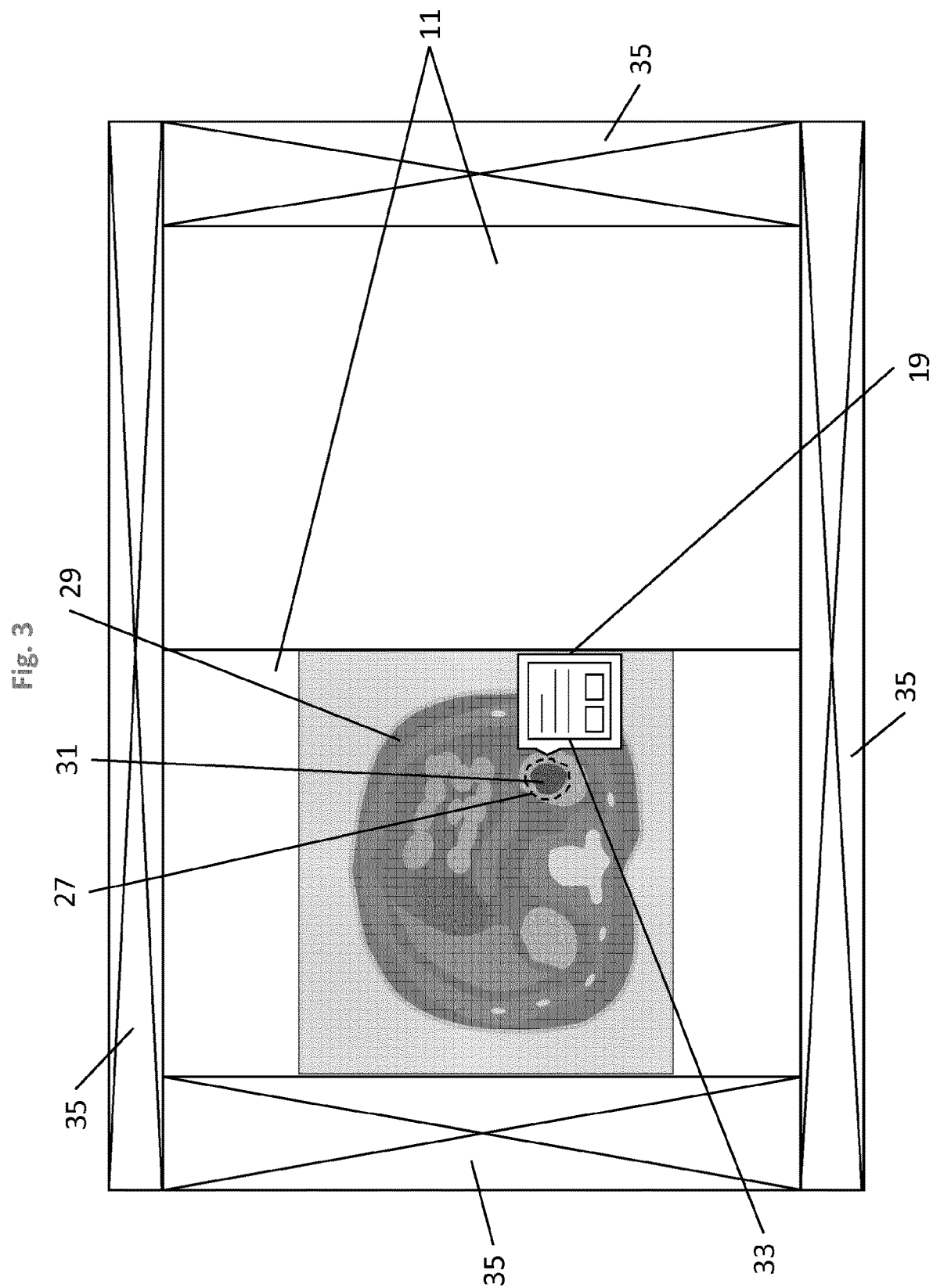
FIG. 3 schematically depicts a non-limiting example of an image display.

According to the above described preferred embodiment, FIG. 3 schematically depicts a non-limiting example of an image display 9. The image display 9 of FIG. 3 comprises two image-display windows 11 that display image content of medical images 3 and four optional image-information sections 35 that may display other relevant information. In this example, only the left image-display window 11 contains image content 29 of the medical images 3. In this example, the image content of the medical images 3 comprises a tomographic slice of a human torso showing, beyond others, the kidneys and a renal cyst 31, muscle, fat, the spine and rib bones, the liver, the gallbladder, the intestine and the pancreas. Also shown in FIG. 3 is an example of a floating UI window 19 that contains context-dependent content 33.

In this example the focus of the user is identified to currently be on the renal cyst 31. Therefore, the active image-display section 27 (indicated by the dashed line) is a region that covers the renal cyst 31, e.g., defined by a mask that results from segmenting the medical images 3.

The content of an image-information section 35 in general includes, but is not limited to, details of series/images, the patient, the protocol and/or viewer options and menus and/or worklists.

Figure 4:
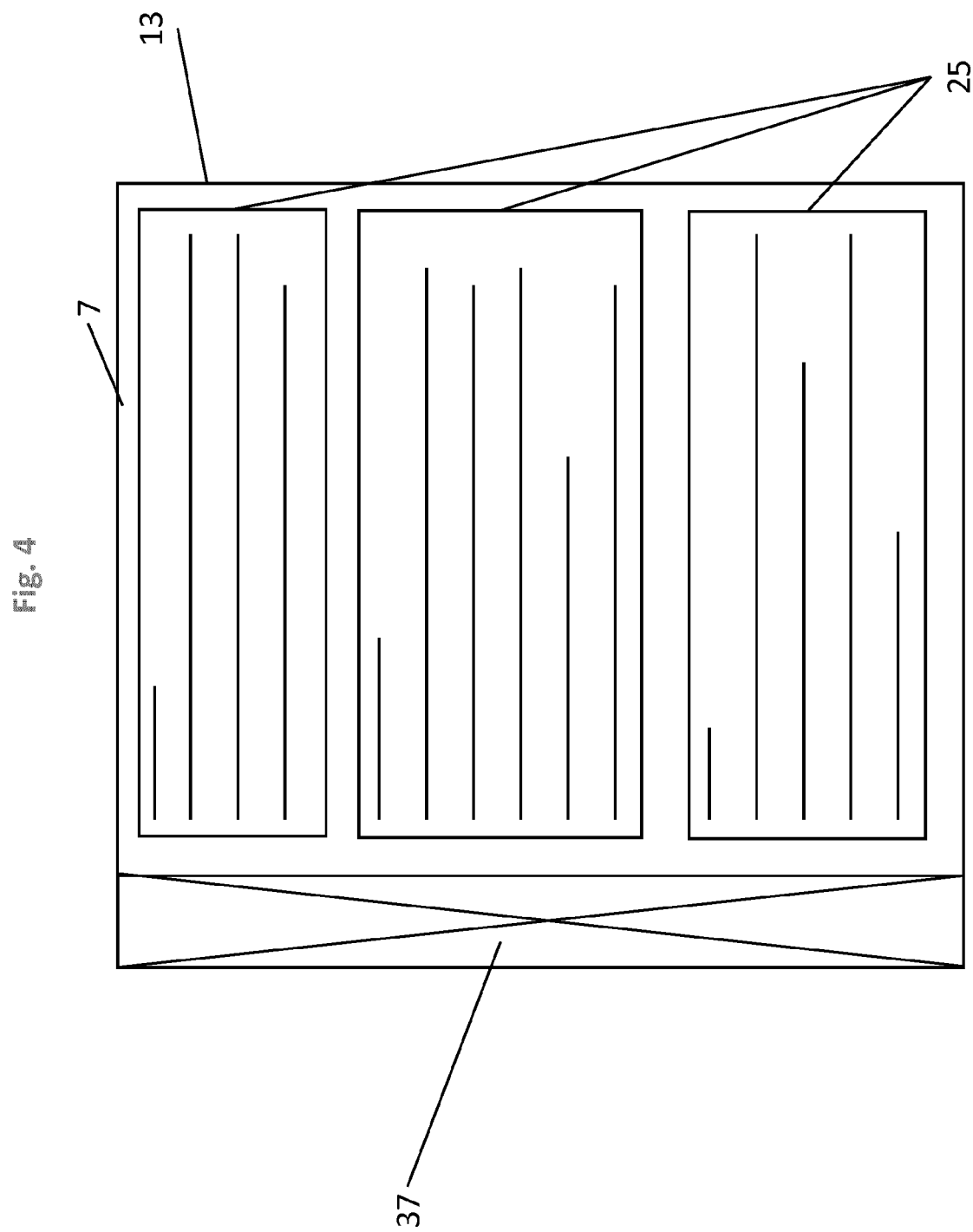
FIG. 4 schematically depicts a non-limiting example of a report display.

According to the above described preferred embodiment, FIG. 4 schematically depicts a non-limiting example of a report display 13. The report display 13 of FIG. 4 contains a machine-readable structured report 7 with three exemplary structured-report elements 25. The report display 13 further contains an optional report-information section 37.

The content of a report-information section 37 in general includes, but is not limited to, worklists, report structure (total or partial visualization of the decision tree used in the structured report), clinical information about the patient and/or protocol, and/or details about series/images.

Figure 5:
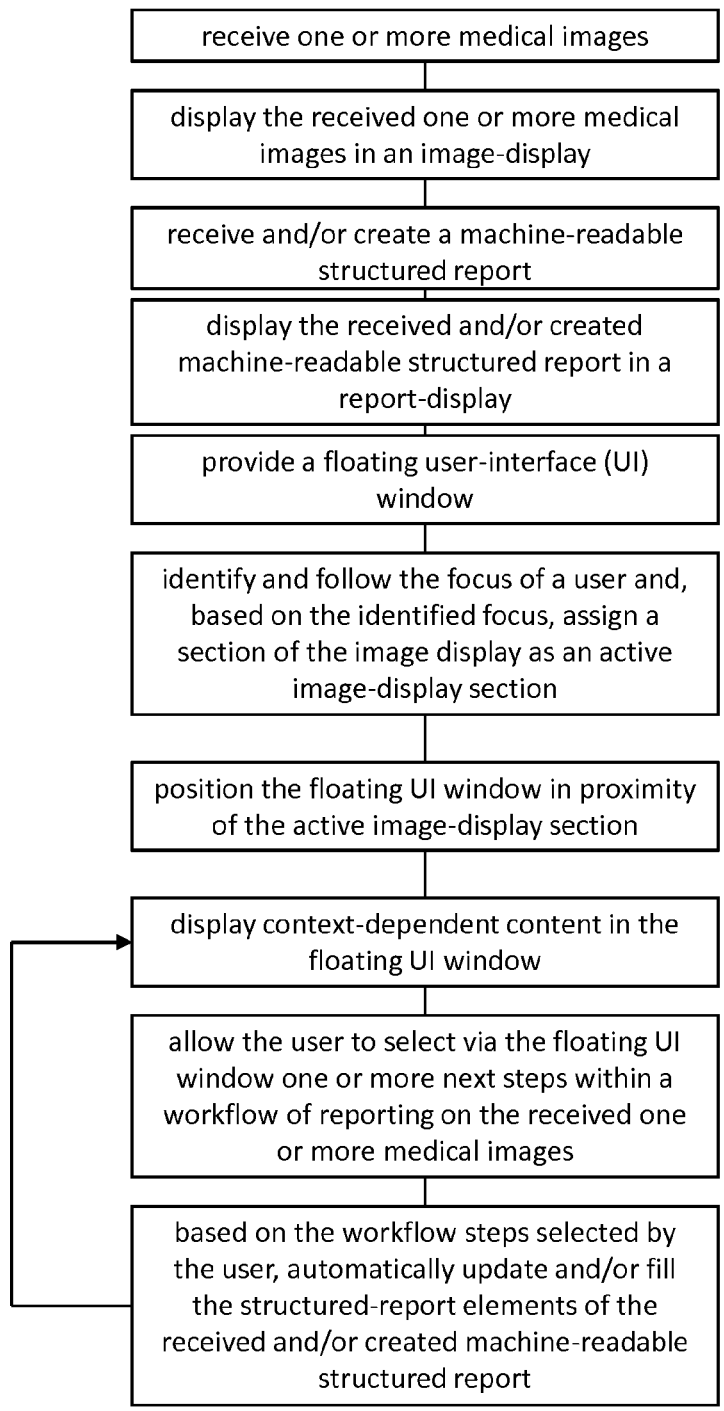
FIG. 5 shows a flow-chart illustrating steps of a method for reporting on medical images.

FIG. 5 schematically depicts in a flow chart the steps of an example for a method for reporting on medical images.

In a first step, one or more medical images 3 are received, e.g. from a PACS or other kind of repository or database located on a server, local computer and/or or storage medium. The one or more medical images 3 can also be obtained directly from an imaging system, e.g. an MRI scanner.

The one or more medical images 3 are then displayed in the image display 9.

Furthermore, one or more machine-readable structured reports 7 are newly created and/or one or more existing ones received and provided. The machine-readable structured reports 7 can, e.g., be received from a RIS or other kind of repository or database located on a server, local computer and/or storage medium.

The machine-readable structured report 7 is displayed in the report display 13.

Further, one or more floating UI windows 19 are provided that contain context-dependent content 33.

The focus of a user is identified and followed. Based on the identified focus, a section of the image display is assigned as an active image-display section 27.

The floating UI window 19 is dynamically positioned such that it appears in proximity to the active image-display section 27.

Context dependent content 33 is displayed in the floating UI window 19.

The user may then interact with the floating UI window 19 or the medical images 3, e.g., by entering values, typing or dictating free text into fields displayed as context dependent content 33 or by creating annotations in the medical images 3. Furthermore, the user can select items presented as context dependent content 33, e.g., items of a drop-down menu or different types of structured elements mentioned before. Some of these items represent next steps that are performed in response to selecting an item. Thus, by selecting items the corresponding steps become part of the workflow of reporting on the received one or more medical images 3.

Based on the interaction of the user with the floating UI window 19 or the medical images 3, the structured-report elements 25 of the machine-readable structured report 7 are automatically updated and/or filled. This may, furthermore, influence the context dependent content 33 of further floating UI windows 19 that are, e.g., provided at a later stage of the workflow of reporting on the medical images 3.

In accordance with other embodiments of the invention, further aspects of the methods and systems with correspondingly configured components are provided. These aspects may be combined with the above described embodiments and comprise additional steps or components configured to carry out these steps. According, to one aspect, positioning of the floating UI window 19 in proximity of the active image-display section 27 further comprises positioning them such that they do not overlap with or otherwise cover the active image-display section 27.

Adapting the position of the floating UI window 19 based on a currently given situation and/or the current position/s of a user's focus reduces the risk of distracting and fatiguing the user. Also, the shape, aspect ratio and/or size of the floating UI window 19, can be adapted dynamically based on the same rules.

FIGS. 12*a*-12*d* show examples of floating UI windows 19 according to the above described further aspects. These floating UI windows 19 are displayed in proximity of the active image-display section 27, but do not cover or overlap with it. The non-limiting examples of indicators that can be used to determine if an image-display section is in an active state and that were discussed earlier in this text also apply here.

FIG. 12*a* illustrates a non-limiting example of a floating UI window 19 according to the above described further aspects that is displayed within the image display and even covering some of the image content of the medical image 3. However, the floating UI window 19 is dynamically adapted to not overlap with the active image-display section 27, i.e., a section of the image display on which user is currently focusing.

FIG. 12*b* shows a non-limiting example of a floating UI window 19 according to the above described further aspects. The floating UI window 19 is positioned in proximity to the active image-display section 27. However, due to the extent of the active image-display section 27, the position of the floating UI window 19 is shifted outside of the medical image 3, i.e., it does in this case not cover the image content of the medical image 3 at all.

FIG. 12*c* shows a non-limiting example of a floating UI window 19 according to the above described further aspects. The floating UI window 19 appears close to the active image-display section 27, but is shifted to a neighboring image-display window 11. The image content of this neighboring image-display window 11 may show a different view of the medical image or even comprise a different medical image 3*a*. However, since the user's focus is currently not on this image and it is in proximity to his or her focus, it is a suitable location for positioning the floating UI window 11.

FIG. 12*d* illustrates a non-limiting example of a floating UI window 19 according to the above described further aspects. In this case the active image display section is relatively large, such that the position of the floating UI window 19 is partly shifted into an image-information section 35. Again, since the user's focus is currently not on the image-information section and it is in proximity to his or her focus, it is a suitable location for positioning the floating UI window 11.

Figure 13:
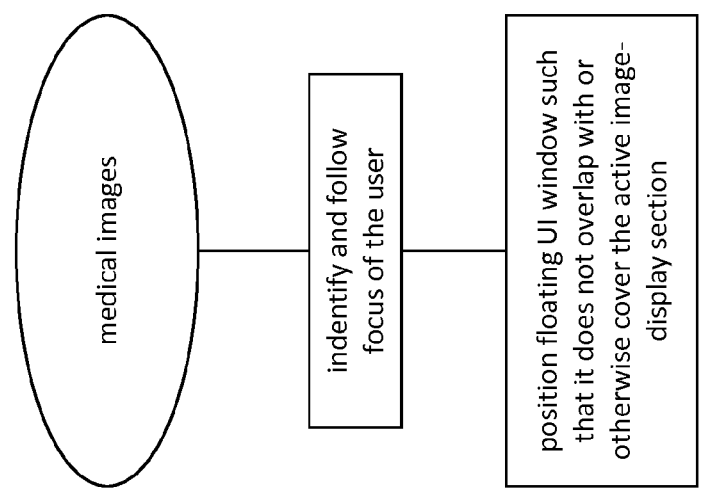
FIG. 13 illustrates exemplary steps of further aspects of a system for reporting on medical images where the floating UI window is dynamically positioned such that it does not cover or overlap with the active image-display section.

FIG. 13 illustrates an example of a method according to the above described further aspects. According to these steps, an image-display section of the image display 9 is determined on which the user is currently focusing and assigned as the active image-display section 27. Criteria for determining positions on which a user is currently focusing on, were discussed earlier in this text and apply here as well.

The floating UI window 19 is then dynamically adapted to be displayed at a position where it does not overlap with or otherwise cover the active image-display section 27. Thus, the floating UI windows 19 may appear within the medical image 3, but do not cover any image content at all or only such that is not in the current focus of the user.

In accordance with other embodiments of the invention, further aspects of methods and systems with correspondingly configured components are provided. These aspects may be combined with the above described embodiments. The methods or systems comprise additional steps or components for carrying out the steps.

According to one aspect, an anatomical location depicted in the active image-display section 27 is identified. Context dependent content 33 whose content depends on the identified anatomical location is then displayed within the floating UI window 17.

According to another aspect, one or more annotations are identified in the received one or more medical images 3. Context dependent content 33 whose content depends on the identified annotations is then displayed within the floating UI window 17.

According to yet another aspect, steps of a workflow that were carried out during the current and/or previous reporting on the medical images are identified in the received and/or created machine-readable structured report 7. Context dependent content 33 whose content depends on the identified workflow steps is displayed within the floating UI window 17.

According to yet another aspect, the specific structure of the received and/or created machine-readable structured report 7 is identified. Context dependent content 33 whose content depends on the identified specific structure is then displayed within the floating UI window 17.

According to yet another aspect, user-selectable presets are identified. Context dependent content 33 whose content depends on the identified user-selectable presets is then displayed within the floating UI window 17.

This improves the usability and ergonomics. The system gathers information, evaluates it taking the given clinical and patient specific context into account and finally brings it into the image display. Consequently, the reviewing physician can be guided and supported while maintaining his or her focus on the image. Compared to the typical clinical setup, where a user has to extract such information her- or himself (often from other sources of information outside of the current image), keep track of it and continuously deduce decisions from it, this is less fatiguing and reduces the risk of eventual errors and impaired efficacy. For example, assume that the system identified a kidney as the anatomical location that a radiologist is currently looking. Via the context dependent content 33 in a floating UI window 19, the system now provides only items that concern a report on a kidney, e.g. renal cyst, renal calculi, renal cell carcinoma, hydronephrosis, as well as other differential diagnoses concerning anatomically close structures, e.g. lymph nodes.

Figure 6:
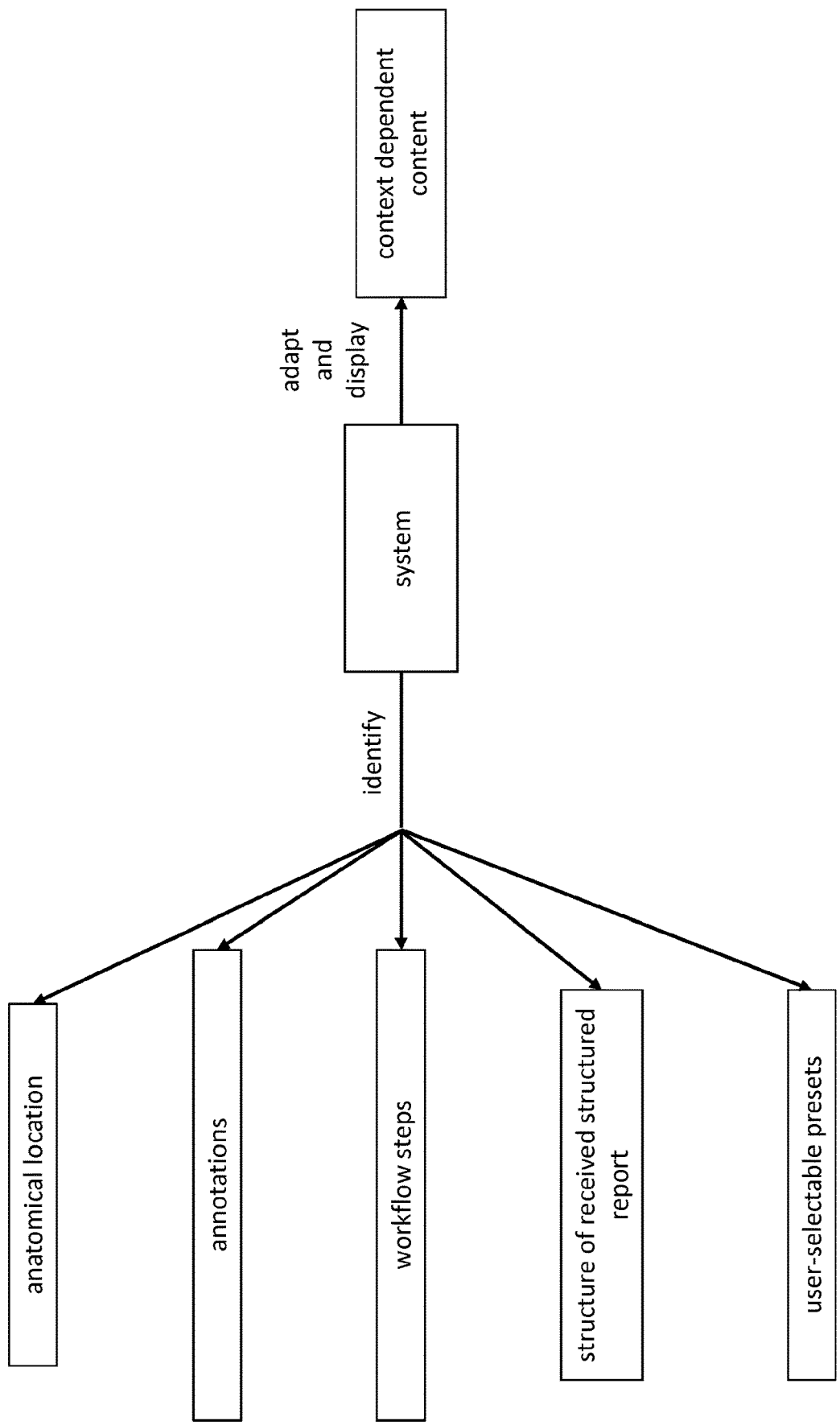
FIG. 6 schematically illustrates further aspects where the system identifies anatomical locations, annotations, workflow steps, structure of received structured report and/or user-selectable presets prior to adapting and then displaying corresponding context-dependent content.

FIG. 6 illustrates an example of a system according to the above described further aspect. In this example, the system identifies one or more anatomical locations, annotations, steps of a workflow, structures of the received machine-readable structured report and/or user-selectable presets. Based on what is identified, the system adapts the context dependent content 33 to it. The system then displays the context dependent content 33.

In accordance with other embodiments of the invention, further aspects of methods and systems with correspondingly configured components are provided. This may be combined with any of the above described embodiments and comprise additional steps or components for carrying out these steps. According to one aspect, information that is relevant for reporting on medical images is extracted from the received medical images 3 and/or the received and/or created machine-readable structured report 7. The extracted information is then displayed as context-dependent content 33 in the floating UI window 19.

For example, such information relevant for reporting on medical images includes, but is not limited to patient-related information like age, gender, clinical history, previous examinations, examinations results, protocols measured for the current and/or previous examinations. Further examples include annotations, details on previous measurements or findings detected by AI.

Figure 7:
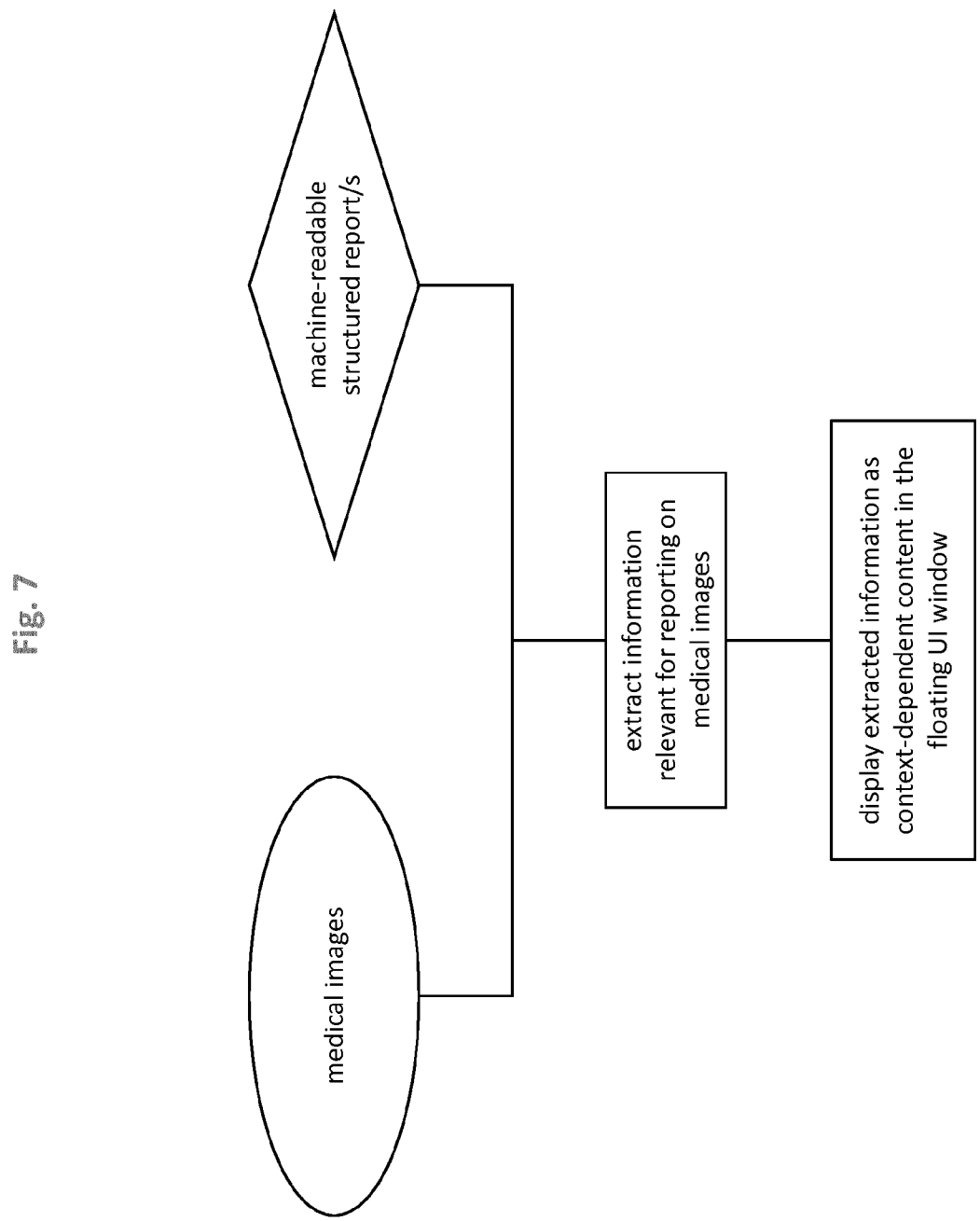
FIG. 7 illustrates further aspects of a system for reporting on medical images where information relevant for reporting on medical images is extracted from existing structured reports and/or from medical images and then displayed as context dependent content.

FIG. 7 illustrates an example of additional steps of a method according to the above described further aspect. Information relevant for reporting on medical images is either extracted from one or more machine-readable structured reports 7 and/or from one or more current or previous medical images 3. As a next step, this information is provided to a user via one or more floating UI windows 19.

In accordance with another embodiment of the invention, further aspects of the methods and systems with correspondingly configured components are provided. These aspects may be combined with the above described embodiments and comprise additional steps or components for carrying out the steps.

According to one aspect, at least some of the annotations is also displayed in the image display 9.

Examples for graphical representations of annotations, include, but are not limited to, ROIs, e.g., for determining mean values, color overlays, e.g. for lesions, color coded information, e.g. on perfusion, visualizations of dynamics, e.g. of blood flow, or text and values, e.g. value of a measured volume.

In a non-limiting example, the image display 9 comprises annotations that were identified in previous machine-readable structured reports and are displayed in the current medical images 3. When the user clicks on and/or otherwise interacts with those displayed annotations the means for providing a floating UI window 17 generates and displays a floating UI window 19, whose context dependent content 33 provides information about the previous and current annotation and/or lesion.

This brings information of former reports and examinations into the displayed medical image, such that a reviewing physician can maintain his or her focus on the medical image while accessing associated information.

Figure 8:
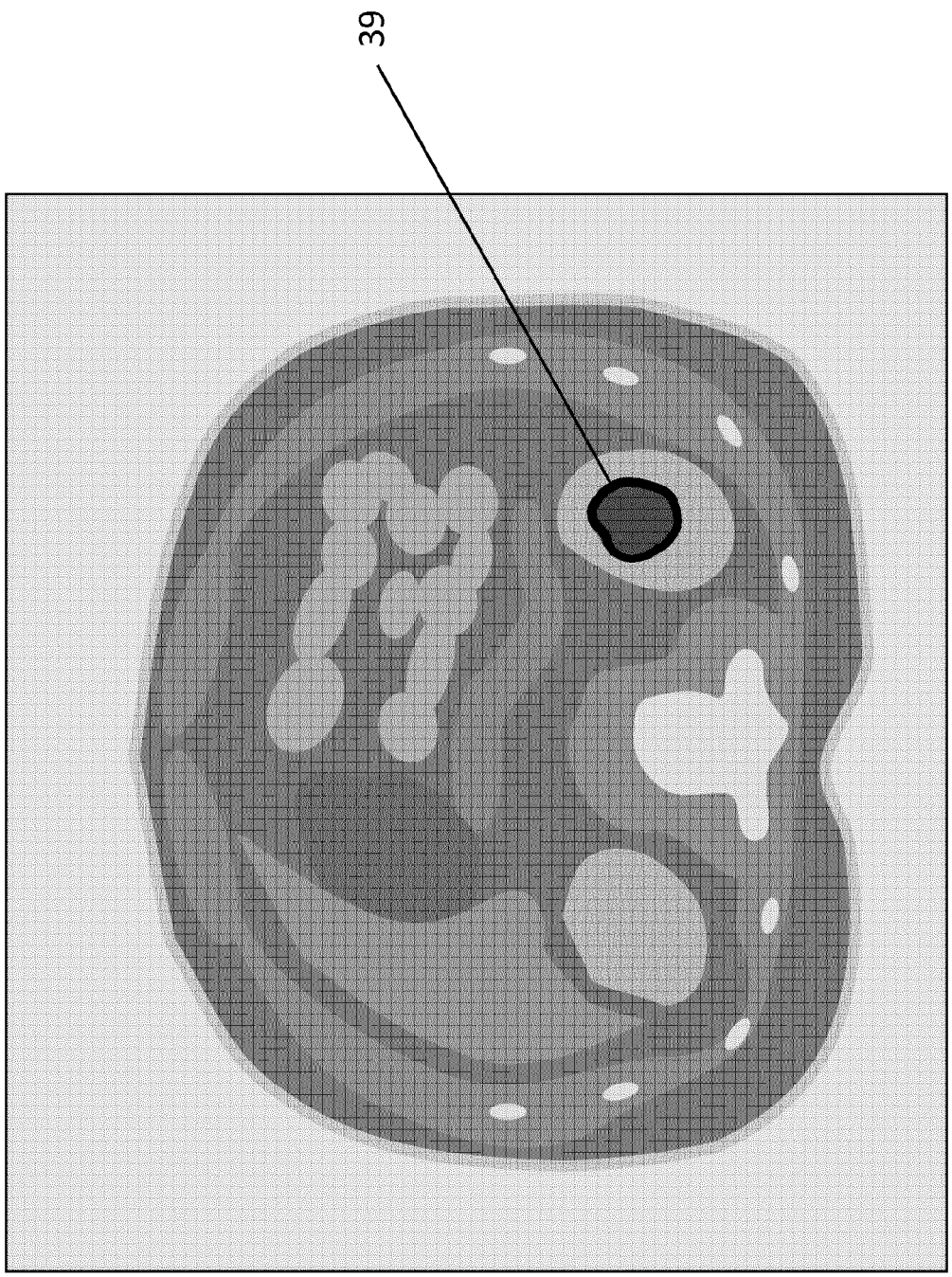
FIG. 8 schematically illustrates an example of further aspects of a system for reporting on medical images where an annotation is displayed within the image display.

FIG. 8 schematically illustrates an example of a system according to the above described further aspect. In this example, an annotation is given by an ROI 39 that covers the extent of a renal cyst. The ROI 39 is displayed as an overlay of the medical image showing an axial slice of a human torso, i.e., it is displayed in the image display 9.

In accordance with other embodiments of the invention, further aspects of the methods and systems with correspondingly configured components are provided. These aspects may be combined with the above described embodiments and comprise additional steps or components for carrying out these steps. According to one aspect, steps that were carried out to make an annotation during a previous reporting on medical images are extracted from the received one or more medical images 3 and/or the received and/or created machine-readable structured report 7. These extracted steps are then displayed as context-dependent content 33 in the floating UI window 19 and as recommendation to include the extracted steps in the workflow.

The steps carried out to make an annotation may, e.g., have been carried out by the radiologist or someone else for a previous report, e.g. as part of reporting on medical images of a previous examination. The details of these steps are then presented to the user such that he or she can reproduce the annotation as exactly as possible for the current report. By presenting this information to the user she or he can comprehend and possibly reproduce previous workflow steps in the current process of reporting. In particular, this reduces a possible intra- or inter-operator bias in follow-up measurements that are carried out, e.g., in order to determine possible growth of a tumor or changes in blood flow dynamics over a period of time.

The recommendation could alternatively or in addition suggest and/or prepopulate metrics for one or more measurements of changes between previous and follow-up examinations.

Figure 9:
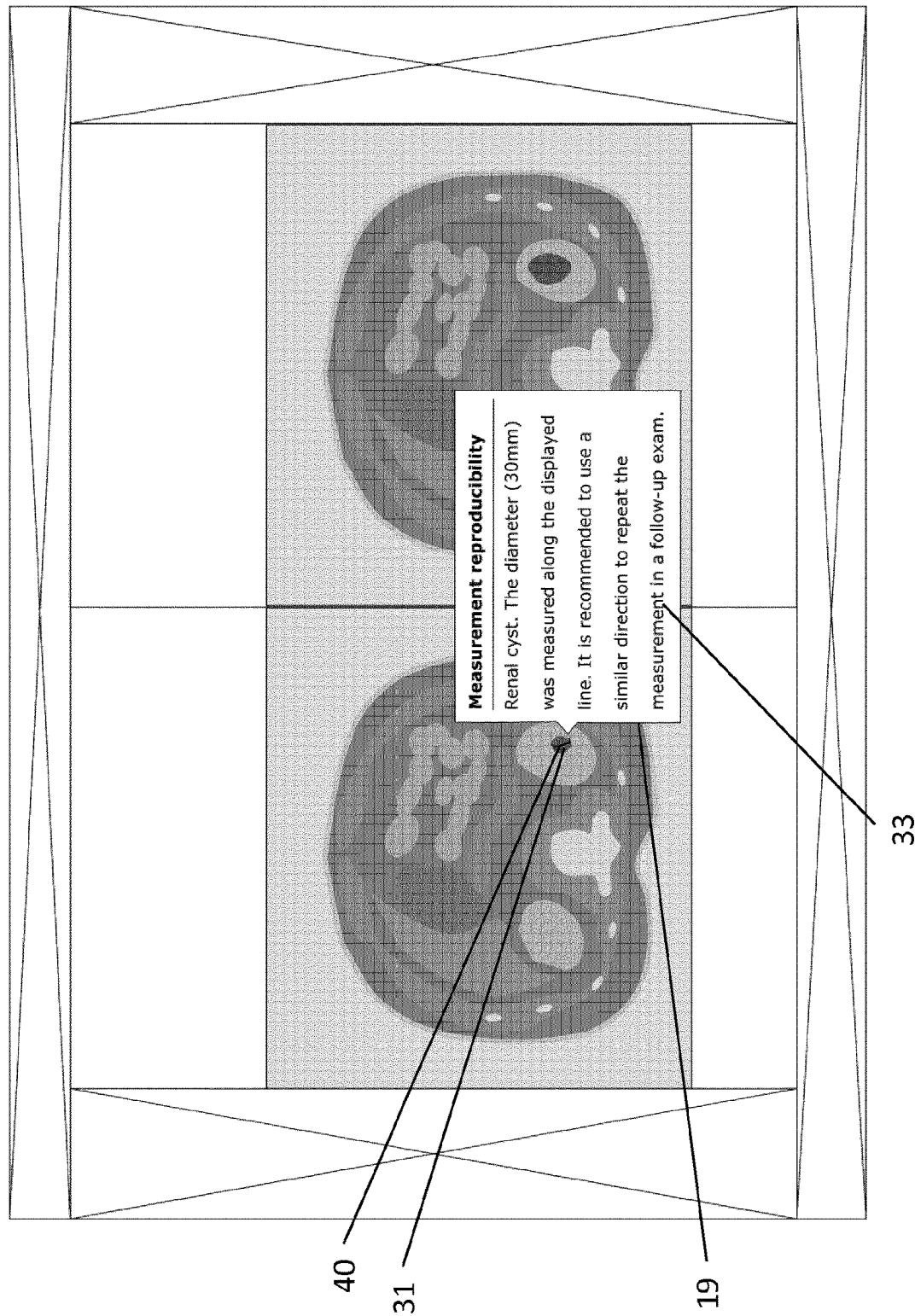
FIG. 9 illustrates an example of a floating UI window that provides the user with information on how a previous measurement, in this case the measurement of the diameter of a renal cyst, was performed

FIG. 9 schematically illustrates an example of a system according to the above described further aspect. In this example, a floating UI window 19 provides the user with information on how a previous measurement was performed, in this case the measurement of the diameter of a renal cyst 31. In this example, the floating UI window 19 contains context dependent content 33 in form of a text that describes the measurement of a previous examination in combination with displaying a graphical element 40, that may itself be considered as a non-limiting example for an annotation and that indicates the position and direction that was used to determine the diameter of the cyst.

Figure 10:
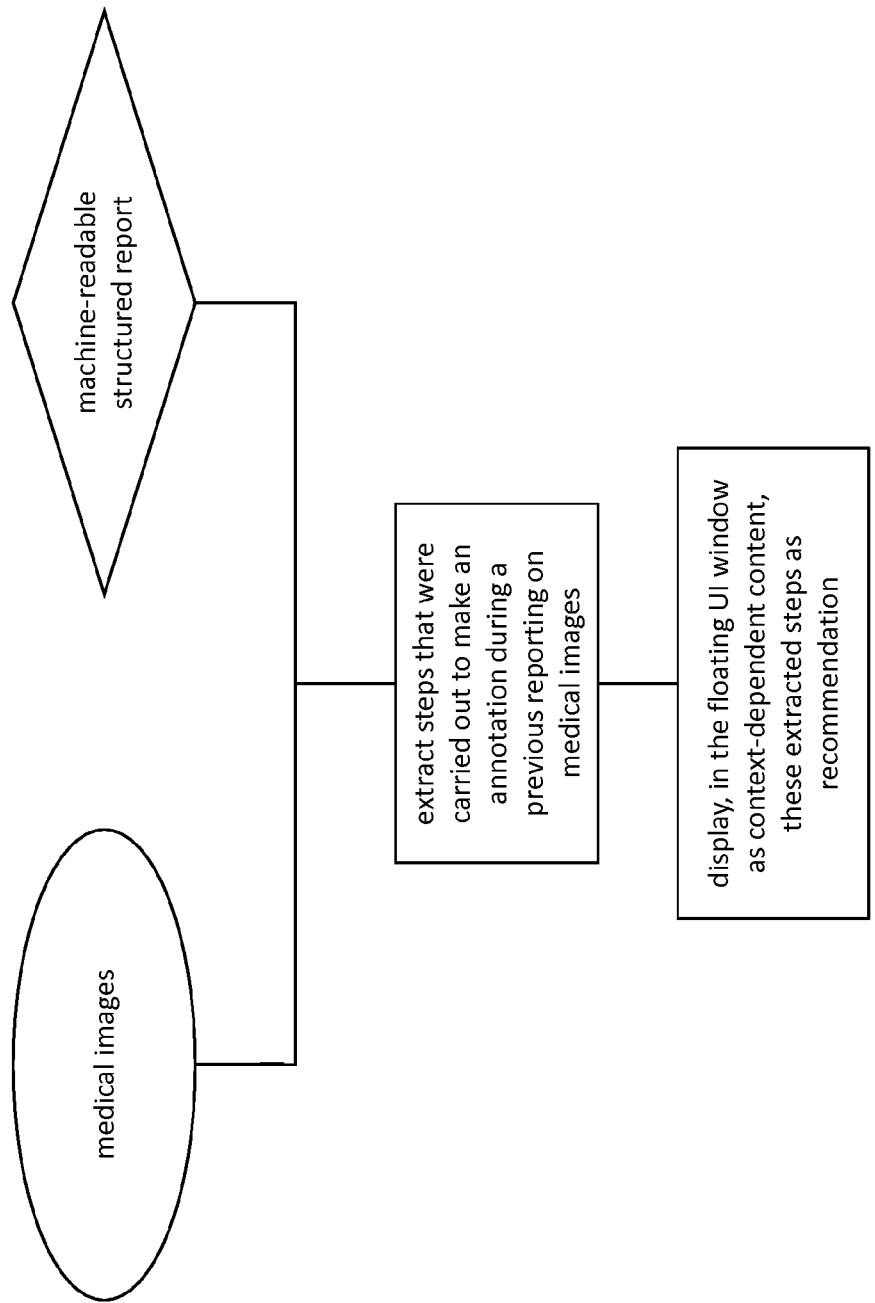
FIG. 10 illustrates an example of, further aspects where steps that were carried out to make an annotation during a previous reporting on medical images are extracted from the received one or more medical images and/or the received and/or created machine-readable structured report and then displayed as recommendation.

FIG. 10 illustrates an example of a method according to the above described further aspects. Steps that were carried out to make an annotation during a previous reporting on medical images are extracted from the received one or more medical images and/or the received and/or created machine-readable structured report. These steps are then presented to the user by displaying them as context dependent content 33 in the floating UI window 19.

In accordance with another embodiment of the invention, further aspects of the methods and systems with correspondingly configured components are provided. These aspects may be combined with the above described embodiments and comprise additional steps or components for carrying out these steps.

According to one aspect, findings made during the reporting on the received one or more medical images 3 are identified. Based on the identified findings, the one or more next workflow steps that are selectable by the user via the floating UI window 17 are adapted.

In general, the adaptation of the one or more next workflow steps may, e.g., be based on statistics from clinical and/or other studies, experience of the current and/or other users and/or common practice as well as any clinical/medical knowledge built in structured report elements.

That way, the radiologist can receive indications for possibly relevant next steps to be included into the workflow and aspects to look at next (workflow with guided navigation through key findings). For example, if a nodule has been measured in the lungs, the floating UI window could suggest giving a closer look to other regions of the lung, as well as adrenal glands and mediastinal lymph nodes, because these regions are known to be prone to metastases from lung tumors. Other examples include colorectal cancer (metastases in lungs, liver), or hepatocellular carcinoma (suggestion of liver cirrhosis, portal hypertension, esophageal varices, ascites). Thus, the floating UI window 19 can be used to display clinical guidance for the radiologist based on key findings (from previous exams or algorithms), medical content saved in database, report structure, or other information. Medical content may for example correspond to decisions trees that were built based on expert knowledge and that constitute the structure of the report for a particular use case/pathology/clinical question. Decision trees summarize the way a radiologist thinks. Further, medical content may for example also or additionally correspond to current clinical guidelines/treatment guidelines/follow-up guidelines, latest research studies and clinical results.

The information necessary for the adaptation may be stored locally on a computer and/or storage medium and/or remotely on a server of an intranet or the internet.

This brings information that is important for the user into the image domain, i.e., the user can maintain his or her focus on the image while receiving the information.

FIG. 11 shows an example of a system according to the above described further aspects. In this example, the floating UI window 19 informs the user via the context-dependent content 33 that the occurrence of a finding of a renal cyst made in the current examination has a significant correlation with the occurrence of cysts in the same or a different anatomical region, in this case typically liver cysts. As a recommendation to the user, the context dependent content 33 offers the option to show further relevant images and to include corresponding workflow steps. In general, the context dependent content 33 may, e.g., contain optional and selectable next workflow steps for reviewing potential other findings in the same or other anatomical regions.

In accordance with other embodiments of the invention, further aspects of the methods and systems with correspondingly configured components are provided. These aspects may be combined with the above described embodiments and comprise additional steps or components for carrying out these steps. According to one aspect, one or more of the structured-report elements 25 with predefined content are automatically filled as a result of the one or more next workflow steps.

This expedites the reporting process and is, therefore, less fatiguing for the user. Furthermore, the user maintains her or his focus on the medical images 3.

For example, the context dependent content 33 of a floating UI window 19 may provide an item that, when selected by a user, annotates a finding as "normal finding" in the machine-readable structured report 7.

In general, the automatic filling of the structured-report elements 25 can be based on trigger signals. Non-limiting examples for trigger signals are combinations of pressed keys on a keyboard (keyboard short-cuts) or voice commands captured by a microphone and processed by a speech recognition engine. Further non-limiting examples include gestures performed with a computer mouse, on a trackpad or on a touch-sensitive screen and/or selectable items or buttons on a dropdown or other type of menu. Yet another non-limiting example for a trigger signal is the creation of an annotation in the medical images 3 and/or an interaction with this annotation by one the means mentioned above. Depending on the specific trigger signal and the context one or more floating UI windows 19 can be displayed. For example, in order to describe a finding as normal a simple double click on an organ can be defined as a trigger signal without using a floating UI window 19. Other trigger signals like specific clicks and/or combinations of keys can trigger displaying a floating UI window 19 that suggests different selectable options and/or presets for filling entries into the structured-report elements 25 associated with this organ, e.g., "normal finding", "normal state after resection of gallbladder" or "no changes since last examination". The absence of any actions can also define a trigger. For example, in the case that no measurement is, performed on an organ, the organ can be annotated as "no findings". The pre-determined content that is transferred to the machine-readable structured report 7 may, e.g., be stored in a repository and/or database located in an intranet, the internet, a storage medium and/or a local computer. The pre-determined content is further associated with the trigger signals such that a matching of the trigger signals to the respective pre-determined content can be performed.

Figure 14:
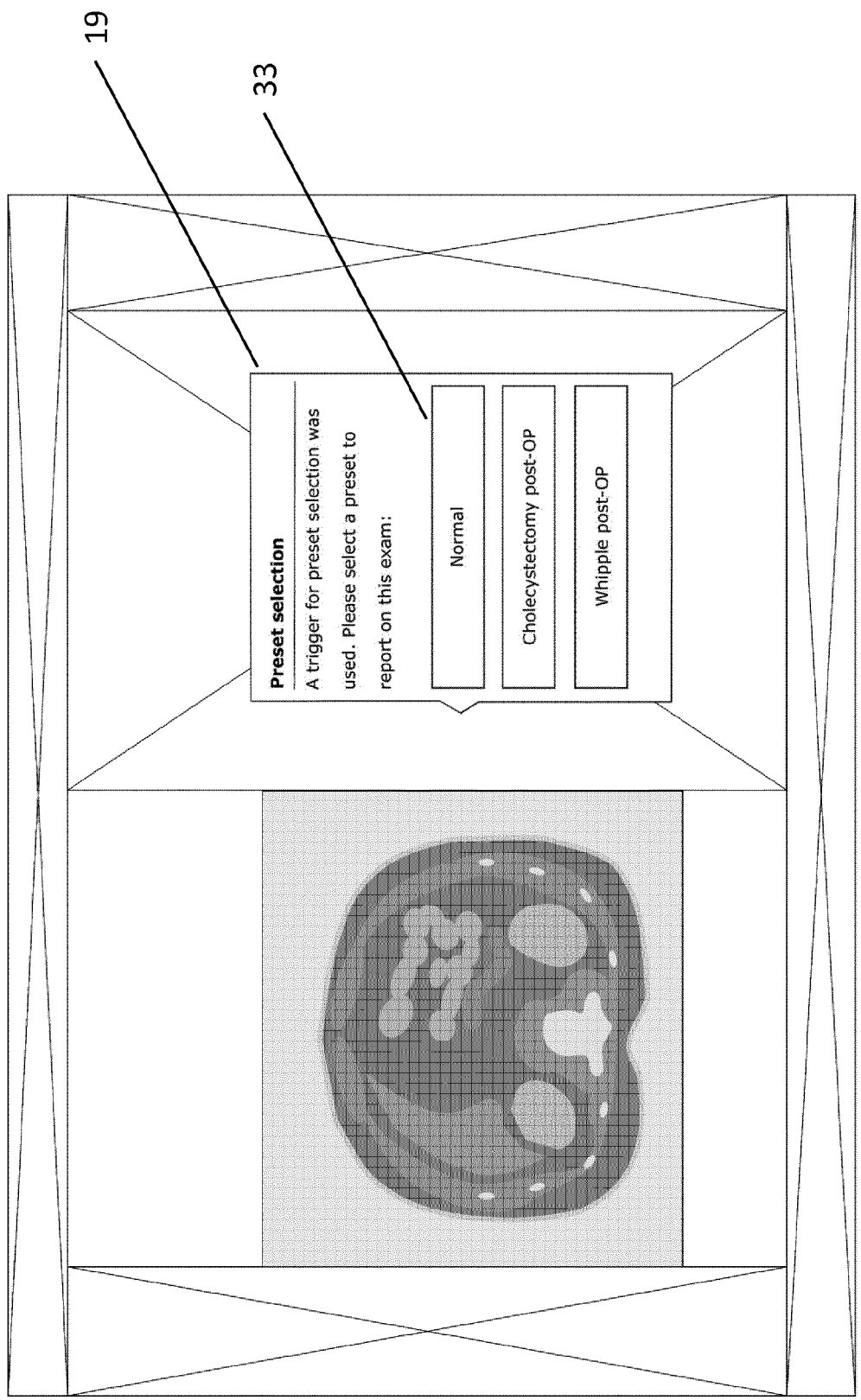
FIG. 14 illustrates an example of a floating UI window that is displayed in response to detecting a trigger signal and provides the option to choose between different presets.

FIG. 14 illustrates an example of a method according to the above described further aspects. In this example, a floating UI window 19 is displayed in response to detecting a trigger signal, e.g. a combination of pressed keys, and provides the option to choose between different presets. In this non-limiting example, the gallbladder as well as the head of the pancreas and part of the duodenum have been removed during a previous OP, called Whipple procedure. In this typical case, the scan cannot be reported using a normal preset because organs are missing. However, other presets can be used for these standard post-OP reports. Selecting one of these presets is provided to the user via the floating UI window's 19 context dependent content 33. The provided selection of presets may be based on clinical information contained in the current or a previous report or the medical images 3, or be based on an AI algorithm that recognized the missing organs and suggested the corresponding optional presets.

Figure 15:
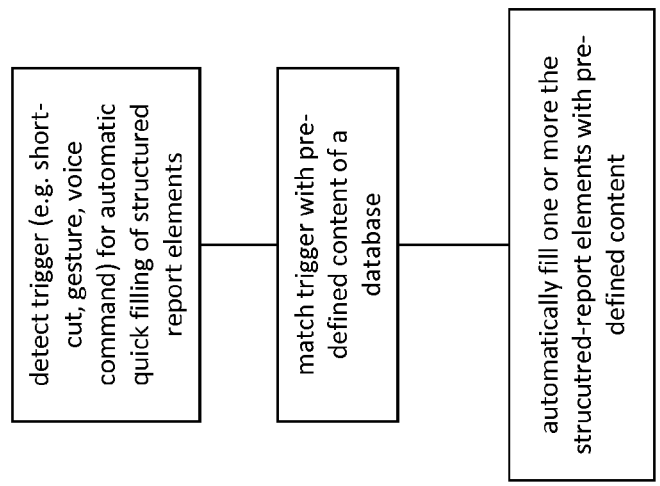
FIG. 15 illustrates exemplary steps of further aspects of a system for reporting on medical images where in response to detection of a trigger signal, structured-report elements may be filled automatically with pre-determined content.

FIG. 15 illustrates an example of a method according to the above described further aspects. According to these steps, if a trigger signal is detected, structured-report elements may be filled automatically with pre-determined content.

In accordance with other embodiments of the invention, further aspects of the methods and systems with correspondingly configured components are provided. These aspects may be combined with the above described embodiments and comprise additional steps or components for carrying out the steps. According to one aspect, additional expert information, such as information from guidelines and/or digital textbooks or reference images, is displayed as context-dependent content 33.

This way, the user can maintain his or her focus on the medical images 3 even when the user wants to refer to external information, i.e., information that cannot be extracted from the medical images or the structured report.

Sources of expert information according to the invention may, e.g., be digital textbooks, guidelines or lexica or suitable combinations thereof. The expert information may be stored on a server in an intranet and/or the internet, on a local computer, and/or a storage medium.

When calculations are required, further context dependent content 33 may be offered to the user, that supports her or him performing these calculations. For example, the functionality of a calculator can be implemented as context depended content 33.

The selectable suggestions for expert information displayed by the floating UI window 19 can also be already sorted in terms of most probable diagnosis for such differential diagnosis cases.

Figure 16A:
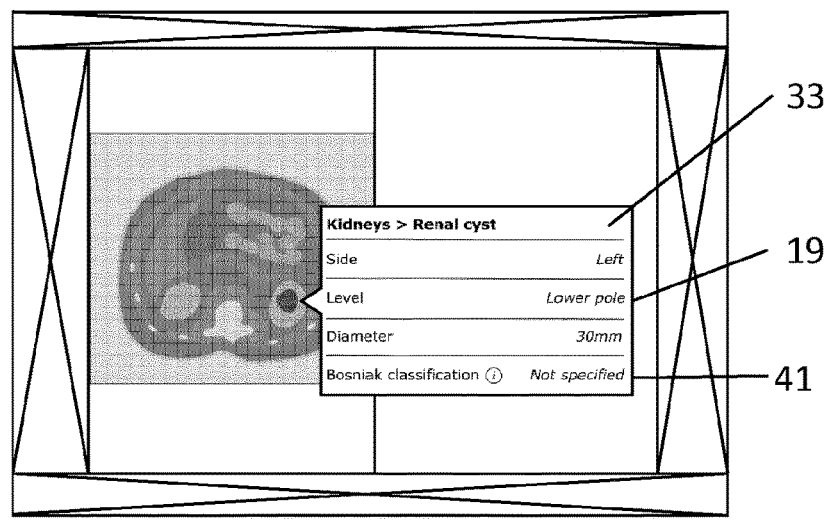
FIGS. 16a-16c schematically illustrate exemplary, but non-limiting, snapshots of a workflow where additional expert information is provided to the user to support a decision.
Figure 16B:
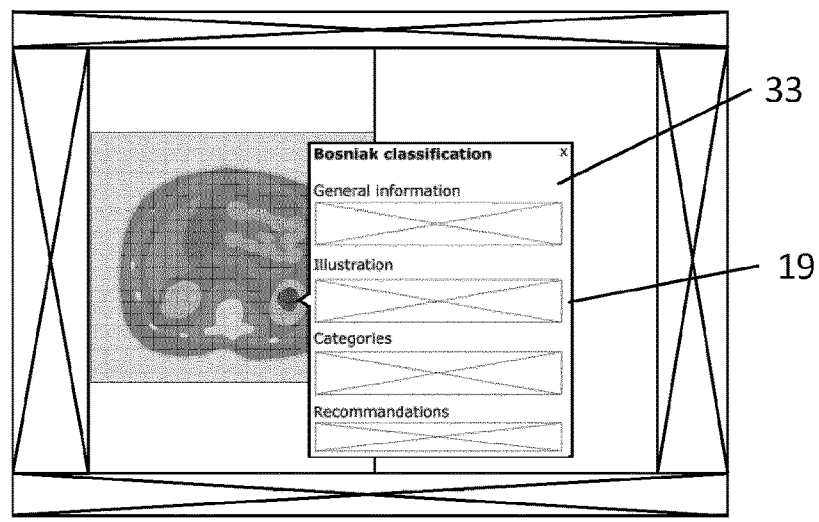

FIG. 16*b* shows an example of a system according to the above described further aspects. Here, the context-dependent content 33 provides expert information on the so-called Bosniak classification of renal cysts.

In general, during reporting, the user may want to refer to information from guidelines, digital textbooks and/or lexica, reference images or content of databases and/or repositories. This information may be stored on the local computer or a server of an intranet or the internet and be made accessible to the user via one or more floating UI windows.

Figure 16C:
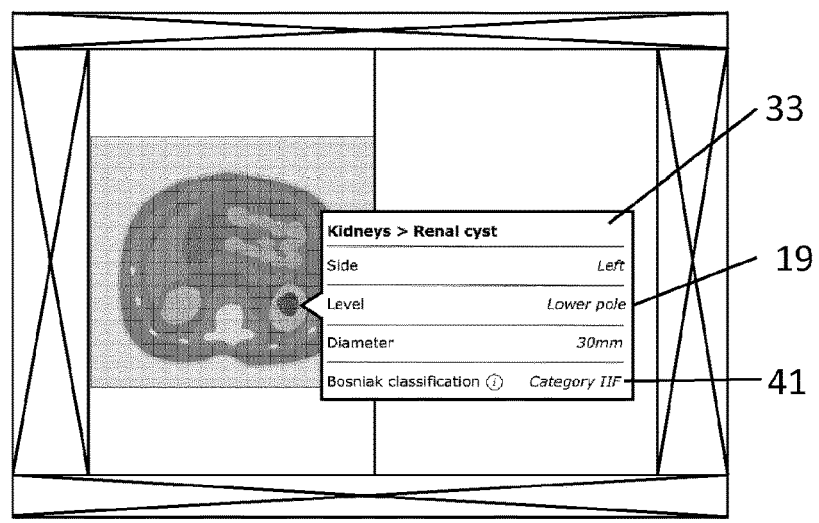

FIGS. 16*a*-16*c* illustrate exemplary, but non-limiting, snapshots of a workflow during which the user accesses expert information that is displayed as context dependent content 33.

In FIG. 16*a* the context dependent content 33 offers an optional field 41 for entering a value for a Bosniak classification of a renal cyst. The context dependent content 33 further offers the radiologist the option to review a guideline on how to determine the correct Bosniak classification (in this example by clicking on the symbol (i)). In general, such guidelines may, e.g., be stored on a server of the clinic's intranet.

In FIG. 16*b* the desired passage of a guideline on determining a Bosniak classification is displayed as context dependent content 33 within the floating UI window 19. The radiologist may then use this information in order to determine the Bosniak classification of the renal cyst.

Finally, as shown in FIG. 16*c*, the radiologist enters the value for the Bosniak classification into the corresponding field 41 provided as context dependent content 33 via the floating UI window 19.

The steps of the above described methods can be executed as computer readable instructions comprised in a computer program product. The computer program product can be stored on a storage medium. Examples for a storage medium include, but are not limited to, a harddrive, a CD or DVD or a Flash Memory. The computer program product can further be loaded, e.g., from an internet- or intranet-server or be electronically transmitted, e.g., via E-mail.

REFERENCE NUMBERS 1 means for receiving medical images
3 medical images
5 means for receiving and/or creating structured reports
7 machine-readable structured report
9 image display
11 image-display window
13 report display
15 report-display window
17 means for providing a floating user interface (UI) window
19 floating user-interface (UI) window
23 means for updating and/or filling structured-report elements
25 structured-report elements
27 active image-display section
31 renal cyst
33 context-dependent content
35 image-information section 37 report-information section
39 region of interest (ROI)
40 graphical element
41 field for entering value of Bosniak classification

What is claimed is:

1. A method for reporting on medical images, the method including steps comprising:
   a) receiving one or more medical images,
   b) receiving or creating a machine-readable structured report,
   c) displaying the received one or more medical images in an image display window being generated and displayed within an image-display,
   d) displaying the received or created machine-readable structured report in a report-display,
   wherein the method further comprises:
      tracking, by identifying and continuously following, the current focus of a user of the method,
      displaying a floating user interface (UI) window in the image display window, wherein a position of the floating UI window is based on the tracked current focus of the user,
      dynamically adapting a position and size of the floating UI window in the image display such
         that the floating UI window is positioned in proximity of a section of the image display window on which the current focus of the user is tracked to be currently located, such that the floating UI window overlaps with the image display window but does not overlap with or otherwise obscure the section, and
         such that the user can look at the floating UI window and interact with the floating UI window while maintaining the current focus;
      displaying context-dependent content in the floating UI window comprising clinically relevant information;
      allowing the user to select via the floating UI window one or more next steps within a workflow of reporting on the received one or more medical images wherein the selectable next-steps are comprised in the context-dependent content; and
      automatically updating or filling the structured-report elements based on the workflow steps selected by the user.

2. The method according to claim 1, wherein the method further comprises extracting, from the received one or more medical images or the received or created machine-readable structured report, steps that were carried out to make an annotation during a previous reporting and displaying, in the floating UI window as context-dependent content, these extracted steps as recommendation to include the extracted steps in the workflow.

3. The method according to claim 1, wherein the method further comprises identifying findings made during the reporting on the received one or more medical images and, based on the identified findings, adapting the one or more next workflow steps that are selectable by the user via the floating UI window.

4. The method according to claim 1, wherein the method further comprises automatically filling, as a result of one or more next workflow steps, one or more of the structured-report elements with predefined content.

5. The method according to claim 1, wherein the method further comprises displaying additional expert-information.

6. The method according to claim 5, wherein the additional expert-information includes information from guidelines or digital textbooks or reference images, as context-dependent content.

7. A computer program product stored on a non-transitory storage medium comprising computer readable instructions that, when executed by a processor, cause the processor to perform steps comprising:
   a) receiving one or more medical images;
   b) receiving or creating a machine-readable structured report;
   c) displaying the received one or more medical images in an image display window being generated and displayed within an image-display;
   d) displaying the received or created machine-readable structured report in a report-display;
   wherein the method further comprises:
      tracking, by identifying and continuously following, a current focus of a user,
      displaying a floating user interface (UI) window in the image display window, wherein a position of the floating UI window is based on the tracked current focus of the user,
      dynamically adapting a position and a size of the floating UI window in an image-display such
         that the floating UI window is positioned in proximity of a section of the image display window on which the current focus of the user is tracked to be currently located, such that the floating UI window overlaps with the image display window but does not overlap with or otherwise obscure the section, and;
         such that the user can look at the floating UI window and interact with the floating UI window while maintaining the current focus;
      displaying context-dependent content in the floating UI window comprising clinically relevant information;
      allowing the user to select via the floating UI window one or more next steps within a workflow of reporting on the received one or more medical images wherein the selectable next-steps are comprised in the context-dependent content; and
      automatically updating or filling the structured-report elements based on the workflow steps selected by the user.

8. The computer program according to claim 7, the steps further comprising extracting, from the received one or more medical images or the received or created machine-readable structured report, steps that were carried out to make an annotation during a previous reporting and displaying, in the floating UI window as context-dependent content, these extracted steps as recommendation to include the extracted steps in the workflow.

9. The computer program according to claim 7, the steps further comprising identifying findings made during the reporting on the received one or more medical images and, based on the identified findings, adapting the one or more next workflow steps that are selectable by the user via the floating UI window.

10. The computer program according to claim 7, the steps further comprising automatically filling, as a result of one or more next workflow steps, one or more of the structured-report elements with predefined content.

11. The computer program according to claim 7, the steps further comprising displaying additional expert-information.

12. The computer program according to claim 11, wherein the additional expert-information includes information from guidelines or digital textbooks or reference images, as context-dependent content.

* * * * *

UNITED STATES PATENT AND TRADEMARK OFFICE
CERTIFICATE OF CORRECTION

PATENT NO. : 12,300,369 B2
APPLICATION NO. : 17/634964
DATED : May 13, 2025
INVENTOR(S) : Alexis Laugerette et al.

Page 1 of 1

It is certified that error appears in the above-identified patent and that said Letters Patent is hereby corrected as shown below:

In the Specification

Column 3, Line 13, "ore" should be --more--.

Column 3, Line 41, "ore" should be --more--.

Signed and Sealed this
Twenty-second Day of July, 2025

Coke Morgan Stewart
*Acting Director of the United States Patent and Trademark Office*